United States Patent [19]

Fischer et al.

[11] 4,338,214

[45] Jul. 6, 1982

[54] MILD-TO-THE-SKIN ANIONIC TENSIDES OF BASIC PROTEIN AMINOLYSATES PREPARATIONS CONTAINING THEM, AND THEIR USE

[75] Inventors: Herbert Fischer; Fanny Scheuermann, both of Düsseldorf; Christian Hase, Erkrath; Horst-Jürgen Krause, Düsseldorf, all of Fed. Rep. of Germany

[73] Assignee: Henkel Kommanditgesellschaft auf Aktien (Henkel KGaA), Dusseldorf-Holthausen, Fed. Rep. of Germany

[21] Appl. No.: 197,650

[22] Filed: Oct. 16, 1980

[30] Foreign Application Priority Data

Nov. 8, 1979 [DE] Fed. Rep. of Germany ....... 2945100

[51] Int. Cl.³ .......................... C07G 7/00; C11D 1/32
[52] U.S. Cl. .................................... 252/545; 252/526; 252/550; 252/554; 252/558; 252/DIG. 1; 252/DIG. 5; 252/DIG. 16; 260/112 R; 260/117; 260/119; 260/123.5; 260/123.7; 424/70
[58] Field of Search ..................... 260/117, 123.7, 119, 260/112 R, 123.5; 252/DIG. 1, 554, 558, 550, 549, DIG. 5, DIG. 1, DIG. 16, 545; 424/70

[56] References Cited

U.S. PATENT DOCUMENTS

| 2,236,271 | 3/1941 | Kratz | 260/119 X |
|---|---|---|---|
| 2,411,019 | 11/1946 | Bersworth | 260/119 X |
| 3,138,581 | 6/1964 | Young et al. | 260/119 X |
| 3,230,210 | 1/1966 | Young et al. | 260/119 X |
| 3,824,228 | 7/1974 | Eckert et al. | 260/112 R |
| 3,904,748 | 9/1975 | Eckert et al. | 424/71 X |
| 4,115,548 | 9/1978 | Marsh et al. | 260/117 X |
| 4,155,882 | 5/1979 | Davies et al. | 252/177 X |
| 4,181,632 | 1/1980 | Schebece | 252/DIG. 16 X |
| 4,195,077 | 3/1980 | Marsh et al. | 260/117 X |
| 4,207,198 | 6/1980 | Kenkare | 252/DIG. 16 X |

FOREIGN PATENT DOCUMENTS 2753850 8/1978 Fed. Rep. of Germany .

*Primary Examiner*—Howard E. Schain
*Attorney, Agent, or Firm*—Hammond & Littell, Weissenberger and Muserlian

[57] ABSTRACT

Mild-to-the-skin salts of anionic tensides of the sulfonate and sulfate type containing as the ion of opposite charge a highly basic protein aminolysate, and their use in washing, rinsing and cleansing compositions as well as in cosmetic preparations which extensively come into contact with the skin.

13 Claims, No Drawings

MILD-TO-THE-SKIN ANIONIC TENSIDES OF BASIC PROTEIN AMINOLYSATES PREPARATIONS CONTAINING THEM, AND THEIR USE

BACKGROUND OF THE INVENTION

The present invention relates to mild-to-the-skin salts of anionic tensides of the sulfonate and sulfate type, particularly alkyl sulfates and ethoxylated alkyl sulfates, containing as the ion of opposite charge (cation) a basic protein aminolysate, their preparation and use in mild-to-the-skin dishwashing, washing and cleaning agents, as well as preparations, particularly cosmetics, containing them.

Efforts to protect material containing keratin, such as skin and hair, against the damaging effects of detergents were initiated long ago, but an entirely satisfactory solution has not been found so far. Numerous possibilities for the solution to these problems have been suggested in the meantime, and especially two different approaches to a solution have been intensively for the anionic tensides, the most widely used class of tensides.

The first approach consists of the addition of products that enhance the skin-preserving aspect, to the anionic tensides such as dishwashing, washing and cleaning agents containing alkyl sulfates or alkyl-lower oxyalkylene-ether sulfates in the form of their alkali metal, amine or alkylolamine salts. Protein substances from any source and in all degrees of chemical modification are used most frequently as such products that enhance the skin-preserving aspect.

The second approach to the improvement of the skin-preserving quality of anionic tensides, particularly alkyl sulfates and alkyl-lower oxyalkylene ether sulfates, is the use of other cations instead of sodium. Here, the diethanolamine and triethanolamine salts of the alkyl and alkylether sulfates have been especially successful. These alkylolamine salts are easier on the skin than the corresponding sodium salts.

OBJECT OF THE INVENTION

An object of the present invention is the obtaining of mild-to-the-skin salts of anionic tensides of the sulfonate and sulfate type containing as the ion of opposite charge a highly basic protein aminolysate.

Another object of the present invention is the obtaining of mild-to-the-skin salts of anionic tensides of the sulfonate and sulfate type containing as the ion of opposite charge for salt formation, a highly basic protein aminolysate obtained by aminolysis of at least one protein with at least one aliphatic, polyamine, having the formula

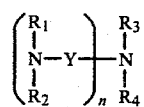

wherein $R_1$ is a peptide radical when n is 1 and, when n is 2 or 3, $R_1$ is a member selected from the group consisting of hydrogen and a peptide radical with a proviso that at least one peptide radical is present, said peptide radical being connected to the nitrogen atom by a carboxyl group of a peptide radical having a molecular weight of from 200 to <5,000;

$R_2$, $R_3$ and $R_4$ are members selected from the group consisting of hydrogen, alkyl having 1 to 4 carbon atoms, alkylol having 2 to 4 carbon atoms, and alkylazaalkyl having 3 to 6 carbon atoms;

Y is an alkylene having from 1 to 4 carbon atoms; and n is an integer from 1 to 3.

A further object of the present invention is the development of washing, rinsing, cleansing and cosmetic compositions characterized by a content of the above mild-to-the-skin salts of anionic tensides.

A yet further object of the present invention is the development of a process for the production of the above mild-to-the-skin salts of anionic tensides consisting essentially of the steps of working intensively together a protein having a molecular weight of from 200 to <5,000 with an aqueous solution of an excess of an amine having the formula

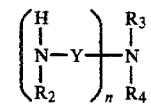

wherein $R_2$, $R_3$ and $R_4$ are members selected from the group consisting of hydrogen, alkyl having 1 to 4 carbon atoms, alkylol having 2 to 4 carbon atoms, and alkylazaalkyl having 3 to 6 carbon atoms;

Y is an alkylene having from 1 to 4 carbon atoms; and n is an integer from 1 to 3, at a temperature of from 70° to 100° C., for a time sufficient to effect substantial aminolysis, precipitation the aminolysate formed, neutralizing said aminolysate with the equivalent amount of an anionic tenside of the sulfonic acid and sulfuric acid half ester type, and recovering said mild-to-the-skin salts.

These and other objects of the invention will become more apparent as the description thereof proceeds.

DESCRIPTION OF THE INVENTION

The drawbacks of the prior art have been avoided and the above objects have been achieved in that new types of tensides have been discovered which passess especially good skin-preserving properties. These are mild-to-the-skin salts of anionic tensides of the sulfonate and sulfate type that contain as the ion of opposite charge for salt formation, a strongly basic protein aminolysate obtained by aminolysis of proteins by means of aliphatic, polybasic amines and having the general formula

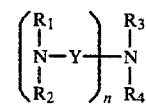

in which $R_1$ represents hydrogen or a peptide radical, with the proviso that at least one of the $R_1$ radicals must be a peptide radical that is connected through the carboxyl group of the peptide radical and has a molar weight of 200 to <5,000; Y represents an alkylene radical with 1 to 4 carbon atoms; $R_2$, $R_3$ and $R_4$ which may be the same or different are hydrogen, an alkyl radical or hydroxyalkyl radical with 1 to 4 carbon atoms, which may be substituted by an amino group, if desired, and n is a number from 1 to 3.

More particularly, the present invention relates to mild-to-the-skin salts of anionic tensides of the sulfonate and sulfate type containing as the ion of opposite charge for salt formation, a highly basic protein aminolysate obtained by aminolysis of at least one protein with at least one aliphatic, polyamine, having the formula

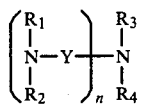

wherein $R_1$ is a peptide radical when n is 1 and when n is 2 or 3, $R_1$ is a member selected from the group consisting of hydrogen and a peptide radical with a proviso that at least one peptide radical is present, said peptide radical being connected to the nitrogen atom by a carboxyl group of a peptide radical having a molecular weight of from 200 to <5,000;

$R_2$, $R_3$ and $R_4$ are members selected from the group consisting of hydrogen, alkyl having 1 to 4 carbon atoms, alkyl having 2 to 4 carbon atoms, and alkylazaalkyl having 3 to 6 carbon atoms;

Y is an alkylene having from 1 to 4 carbon atoms; and n is an integer from 1 to 3.

Of the above novel tensides, those having special significance have a protein aminolysate serving as the ion of opposite charge for salt formation which has a peptide radical with a molar weight of 500 to 5000, especially 500 to 1,000.

The acid anionic tensides that lead to the novel tensides via the neutralization with the protein aminolysates are mainly organic sulfuric acid reaction products containing in their molecular, in addition to a sulfonate or sulfate group, an alkyl group with 8 to 22 carbon atoms, an alkylbenzene group with 9 to 15 carbon atoms in the alkyl group, an alkylglyceryl ether group with a higher alkyl group with 8 to 22 carbon atoms, a fatty acid monoglyceride group, an alkylphenolethylene oxide ether group with 1 to 12 ethylene oxide units and an alkyl radical with 8 to 18 carbon atoms, an alkylethylene oxide ether group with 1 to 30 ethylene oxide units and an alkyl radical with 8 to 24 carbon atoms. The alkyl monoesters of sulfuric acid or alkylether monoesters of sulfuric acid with an alkyl chain of 8 to 18 carbon atoms are of special importance here.

The starting proteins, which yield the protein aminolysates to be used according to the invention after the appropriate treatment, are all natural, synthetic or biosynthetic proteins such as keratin, fibrinogen, skin protein, gelatine, whey protein, casein, soy protein, peanut protein, cotton seed protein, polylysine, proteins obtain from microorganisms, etc. Preferably, the proteins have molecular weights of from 200 to over 5000 although high molecular weight proteins may be employed where, during aminolysis, the molecule is degraded to a molecule within the molecular weight range of 200 to 5000. Gelatin, casein and skin protein are of special importance as starting proteins.

The novel tensides according to the invention are prepared by working together intensely the protein used as starting material with an excess of the aqueous solution of the aliphatic, polybasic amine for a prolonged period of time at an elevated temperature of about 70° to 100° C., precipitating the obtained aminolysate and freeing it from excess amine, and subsequently neutralizing the highly basic protein aminolysate which remains, with the equivalent amount of alkyl monosulfate or alkylether monosulfate. Aliphatic, polybasic amines to be used for the aminolysis of the protein are alkylene di-, tri- and tetramines, ethylene diamine and diethylene triamine being the most important.

Consequently, the preferred tensides according to the invention are neutral salts of alkyl monosulfates or alkylether monosulfates, the alkyl chain of which has 8 to 18 carbon atoms with protein aminolysates obtained by the aminolysis of gelatin, casein or skin protein with ethylene diamine or diethylene triamine.

Another subject of the invention is the use of the novel tensides according to the invention in dishwashing, washing and cleaning agents which are mild-to-the-skin as well as cosmetic preparation. As types of such mild cleaning agents may be mentioned washing agents for the hand wash in the washbasin, as well as mainly cosmetic cleansers such as bath and shower products and hair shampoos, besides dishwashing agents. The novel tensides according to the invention are used in the regular manner in the mentioned products in place of the tensides included until now.

Dishwashing, washing and cleaning agents, particularly cosmetic preparations containing the tensides according to the invention, are another object of the invention. The content of the tensides according to the invention in these mild dishwashing agents, agents for handwashables, bath and shower products and hair shampoos is generally between 10% and 70% by weight, calculated for the total preparation. The preparations also contain the components normally used in such products. Beside their special skin-protecting characteristic, the tensides according to the invention are particularly suitable as starting materials for liquid cosmetic cleansing preparations because they produce light yellow solutions of relatively low viscosity in water that are very compatible with the other components, are easy to incorporate into cosmetic formulations and have a long shelf-life.

The examples below shall explain the subject of the invention in more detail without limiting it to them, however.

EXAMPLE 1

Preparation of the Novel Tensides According to the Invention 150 gm of the protein substance listed in Table I below were mixed with the amount of amine listed there and with 40 gm water in a kneader and mixed for 2 hours at 95° C. The viscous mass obtained was poured into 1 liter of isopropanol, whereupon the formed aminolysate precipitated. This aminolysate was purified by redissolving several times in water, reprecipitated with isopropanol, and then dried. The amounts of aminolysate recorded in Table I were obtained.

TABLE I

| Product | Protein | Ethylene diamine gm | Diethylene-triamine gm | Yield aminolysate gm | Molar wt. aminolysate | Mmol basic amino group per gm aminolysate |
|---|---|---|---|---|---|---|
| A | Gelatin | 60 | — | 106 | 650 | 1.68 |

TABLE I-continued

| Product | Protein | Ethylene diamine gm | Diethylene-triamine gm | Yield aminolysate gm | Molar wt. aminolysate | Mmol basic amino group per gm amino-lysate |
|---|---|---|---|---|---|---|
| B | Casein | — | 51 | 119 | 760 | 3.5 |
| C | Gelatin | — | 69 | 119 | 915 | 1.82 |
| D | Casein | — | 69 | 130 | 560 | 3.85 |
| E | Gelatin | 20 | — | 90 | 550 | 1.51 |
| F | Skin protein | 40 | — | 100 | 785 | 1.87 |

The isopropanol-free aminolysate obtained was dissolved in water to give a 25% by weight solution and neutralized with the amount of alkylether monosulfate given in Table II, while stirring with a fast agitator. A $C_{12}$–$C_{14}$-fatty alcohol-ether monosulfate with two ethylene oxide (EO) groups in the molecule was used as the alkylether monosulfate. All basic amino groups in the tensides obtained according to the invention were neutralized; the products in the aqueous solution have a pH of 6.5–7. The concentration of the obtained aqueous tenside solution is recorded as well in Table II.

TABLE II

| Product | Amino-lysate gm | Alkylether Monosulfate gm | Concentration of tenside % |
|---|---|---|---|
| A | 106 | 50 | 34 |
| B | 119 | 120 | 44 |
| C | 119 | 57 | 37 |
| D | 130 | 139 | 41 |
| E | 90 | 36 | 32 |
| F | 100 | 53 | 34 |

The zein test was used to determine the skin-protective quality of the novel tensides according to the invention. The test product was the neutralization product of fatty alcohol-$C_{12}$–$C_{14}$-ether monosulfate with the aminolysate of casein+diethylene triamine with the molar weight 670. Comparison substances were nonylbenzene sulfonate (Na-salt), sodium lauryl sulfate (Na-salt) and sodium lauryl ether sulfate with 2 ethylene oxide groups in the molecule (Na-salt).

The zein number obtained in the zein test indicates how many mg of nitrogen are contained in 100 ml of a tenside solution, when this is reacted with 2 gm of zein for 1 hour at 35° C. The lower the zein number, the better the product will be tolerated by the skin. The zein test is performed in the manner described below.

1. Preparing the Stock Solutions:

1.1 Sodium Hydroxide Solution 1/20 N

The 1/20 N sodium hydroxide solution was adjusted with benzoic acid (DAB 6 German Pharmacopeia). Approx. 40 to 50 mg of benzoic acid were weighed into a 100 ml Erlenmeyer flask and dissolved in approximately 25 ml of neutralized ethyl alcohol. For the neutralization, the alcohol was mixed with several drops of dilute sodium hydroxide solution against phenolphthalein until the solution remained pink. The dissolved benzoic acid was then titrated with the 1/20 N sodium hydroxide solution until the solution remains pink and the factor is calculated:

1 ml 1/20 N NaOH=6.1 mg benzoic acid 1.2 Sulfuric Acid 1/20 N

A microburet was used to delivery 10 ml of the 1/20 N sulfuric acid into a 100 ml Erlenmeyer flask, 5 drops of Tashiro indicator were added and the receiver was attached to the distilling apparatus. The distilling flask were charged with 20 ml of 25% sodium hydroxide solution, diluted with distilled water to one-half of the volume and distilled for 7 to 10 minutes. The receiver was removed and, after rinsing off the glass tube immersed in the sulfuric acid with some distilled water, the solution was titrated with 1/20 N sodium hydroxide solution from violet to blue-green. The obtained value is the blank value, which is at the same time a control of the distilling apparatus and is determined regularly. The calculation of the nitrogen content is based on this number.

1.3 Tashiro indicator 0.24 gm of methyl red in 300 ml of ethanol and 0.40 gm of methylene blue in 400 ml of 50% ethanol.

1.4 25% Sodium Hydroxide Solution from NaOH pellets 1.5 The tenside to be tested was made up as a solution of x% with distilled water and adjusted to a pH of 7.

2. Preparation of the Zein

The zein from corn (MW 20,000–30,000; ~98.5% protein) was dried in the vacuum drying oven at 40° C. max. until the weight was constant.

3. Performing the Test 40 ml of the tenside solution were pipetted into a 50 ml narrow mouth bottle with screw top and warmed to 35° C. in a water bath. Two grams of zein were weighed accurately on cardboard and quickly dropped into the bottle through a funnel of photographic paper and immediately vigorously shaken 25 times by hand so that the zein was well distributed without clumping.

Several bottles can be fastened in a Wacker apparatus that has an air temperature adjusted to 35° C. and contains steel attachments with springs for this purpose, where they were then rotated at 5 rpm for one hour. Then, an aliquot of the solution (approx. 25 ml) was weighed into a centrifuge beaker of V2A-steel and centrifuged at 2,600 rpm for 30 minutes. Approx. 10 ml were now filtered through a fluted filter (Schleicher & Schüll, No. 597 ½ black band, φ5.5 cm) into a 50 ml Erlenmeyer flask. The nitrogen content of this solution was determined in duplicate by the Micro-Kjeldahl method.

One milliliter of the yellow solution (2 to 5 ml are used of very weakly colored solutions) was reacted with a small amount of selenium reaction mixture and approximately 3 ml of conc. sulfuric acid in a 100 ml Kjeldahl flask. The flask was placed in the electro-thermal apparatus (the flasks must be clean and dry on the outside and no solution may drip into the heating aggregates) and digested in the heat for approximately 2½–3 hours, until the liquid was as clear as water.

The cooled solution was then transferred to a distillation apparatus, mixed with 20 ml of a 25% sodium hydroxide solution and several drops phenolphthalein. It must be ascertained that the sample solution actually is alkaline. The flask may be only about one half full. The ammonia was now distilled with steam, over a period of 7-10 minutes (longer if necessary, test with pH paper), into a receiver containing 10 ml of 1/20 N sulfuric acid and about 10 ml of distilled water. The acid used up by the distilled-over ammonia was calculated by back-titration of the unused sulfuric acid in receiver with 1/20 N sodium hydroxide solution against the Tashiro indicator and the nitrogen was taken up was determined from it:

$$1 \text{ ml } 1/20 \text{ n } H_2SO_4 \triangleq 0.7 \text{ mg N}.$$

The nitrogen content of tensides already containing nitrogen was also determined by the Micro-Kjeldahl method and subtracted from the final result for the calculation.

The zein numbers compiled in Table III below, which show the very good skin-protective quality of the tensides according to the invention, were obtained in the zein test.

TABLE III

| Substance | Zein number |
|---|---|
| nonylbenzene sulfonate, 20% | 620 |
| sodium lauryl sulfate, 20% | 535 |
| sodium lauryl ether sulfate, 20% | 288 |
| sodium lauryl ether sulfate, 5% | 113 |
| sodium lauryl ether sulfate, 1% | 13 |
| neutralization product according to the invention, 20% | 25 |

Several examples for cleaning agents with a content of the tensides according to the invention are given below:

EXAMPLE 2

Cleaning Agent

20% Product A (neutralization product of $C_{12}-C_{14}$-fatty alcohol + 2EO monosulfate with the gelatin-/ethylene diamine aminolysate)
25% tripotassium orthophosphate
0.1% perfume oil
remainder—water.

EXAMPLE 3

Cleaning Agent

15% Product B (neutralization product of $C_{12}-C_{14}$-fatty alcohol+2EO monosulfate with casein/diethylene triamine aminolysate)
10% urea
5% ethanol
0.1% perfume oil
remainder—water

EXAMPLE 4

Bubble Bath

35% Product C (neutralization product of $C_{12}-C_{14}$-fatty alcohol+2EO monosulfate with gelatin/diethylene triamine aminolysate)
5% of diethanolamide of coconut fatty acids
3% perfume oil
57% water

EXAMPLE 5

Shower Bath

30% Product D (neutralisation product of $C_{12}-C_{14}$ fatty alcohol+2 EO-monosulfate with casein/diethylene triamine aminolysate)
3% monoethanolamide of coconut fatty acids
5% diethanolamide of coconut fatty acids
2% perfume oil
60% water

EXAMPLE 6

Baby Bubble Bath

60% Product E (neutralization product of $C_{12}-C_{14}$-fatty alcohol+2EO monosulfate with gelatin/ethylene diamine aminolysate)
15% caprylic/capric acid triglyceride
3% camomile extract
1% perfume oil
21% water.

EXAMPLE 7

Hair Shampoo

20% Product F (neutralization product of $C_{12}-C_{14}$-fatty alcohol+2EO monosulfate with skin protein/ethylene diamine aminolysate)
6% monoethanolamide of coconut fatty acids
2% perfume oil
72% water The preceding specific embodiments are illustrative of the practice of the invention. It is to be understood however, that other expedients known to those skilled in the art or disclosed herein may be employed without departing from the spirit of the invention or the scope of the appended claims.

We claim:

1. Mild-to-the-skin salts of anionic tensides of the sulfonic acid and sulfuric acid half ester type containing as the ion of opposite charge for salt formation, a highly basic protein aminolysate obtained by aminolysis of at least one protein with at least one aliphatic polyamine, said protein aminolysate having the formula $$\left( \begin{array}{c} R_1 \\ | \\ N-Y \\ | \\ R_2 \end{array} \right)_n \begin{array}{c} R_3 \\ | \\ N \\ | \\ R_4 \end{array}$$

wherein $R_1$ is a peptide radical when n is 1 and, when n is 2 or 3, $R_1$ is a member selected from the group consisting of hydrogen and a peptide radical with a proviso that at least one peptide radical is present, said peptide radical being connected to nitrogen atom by a carboxyl group of a peptide radical having a molecular weight of from 200 to <5,000;

$R_2$, $R_3$ and $R_4$ are members selected from the group consisting of hydrogen, alkyl having 1 to 4 carbon atoms, alkylol having 2 to 4 carbon atoms, and alkylazaalkyl having 3 to 6 carbon atoms;

Y is an alkylene having from 1 to 4 carbon atoms, and n is an integer from 1 to 3.

2. The mild-to-the-skin salts of anionic tensides of claim 1 wherein said peptide radical $R_1$ has a molecular weight of from 200 to 5000.

3. The mild-to-the-skin salts of anionic tensides of claim 1 wherein said peptide radical $R_1$ has a molecular weight of from 500 to 1000.

4. The mild-to-the-skin salts of anionic tensides of claim 1 wherein said anionic tensides of the sulfonic acid and sulfuric acid half ester type are selected from the group consisting of alkyl monoesters of sulfuric acid having from 8 to 18 carbon atoms and alkyl ethylene oxide ether monoesters of sulfuric acid having from 8 to 18 carbon atoms in the alkyl and from 1 to 30 ethylene oxide units.

5. The mild-to-the-skin salts of anionic tensides of claim 1 or 3 or 4 wherein said at least one protein is selected from the group consisting of gelatin, skin protein and casein.

6. The mild-to-the-skin salts of anionic tensides of claim 1 or 3 or 4 wherein said at least one aliphatic polyamine is a member selected from the group consisting of ethylene diamine and diethylene triamine.

7. Mild-to-the-skin salts of anionic tensides selected from the group consisting of alkyl monoesters of sulfuric acid having from 8 to 18 carbon atoms and alkyl ethylene oxide ether monoesters of sulfuric acid having from 8 to 18 carbon atoms in the alkyl and from 1 to 30 ethylene oxide units, containing as the ion of opposite charge for salt formation, a highly basic protein aminolysate obtained by aminolysis of a protein selected from the group consisting of gelatin, skin protein and casein with an aliphatic polyamine selected from the group consisting of ethylene diamine and diethylene triamine, the peptide radicals in said protein aminolysate having a molecular weight of from 500 to 1000.

8. A process for the production of the mild-to-the-skin salts of anionic tensides of claim 1 consisting essentially of the steps of working intensively together a protein having a molecular weight of from 200 to <5000 with an aqueous solution of an excess of an aliphatic polyamine having the formula

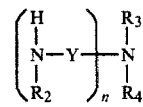

$R_2$, $R_3$ and $R_4$ are members selected from the group consisting of hydrogen, alkyl having 1 to 4 carbon atoms, alkylol having 2 to 4 carbon atoms, and alkylazaalkyl having 3 to 6 carbon atoms;

Y is an alkylene having from 1 to 4 carbon atoms; and n is an integer from 1 to 3, at a temperature of from 70° to 100° C., for a time sufficient to effect substantial aminolysis, precipitation the aminolysate formed, neutralizing said aminolysate with the equivalent amount of an anionic tenside of the sulfonic acid and sulfuric acid half ester type, and recovering said mild-to-the-skin salts.

9. The process of claim 8 wherein said anionic tensides of the sulfonic acid and sulfuric acid half ester type are selected from the group consisting of alkyl monoesters of sulfuric acid having from 8 to 18 carbon atoms and alkyl ethylene oxide ether monoesters of sulfuric acid having from 8 to 18 carbon atoms in the alkyl and from 1 to 30 ethylene oxide units.

10. The process of claim 8 wherein said protein is selected from the group consisting of gelatin, skin protein and casein.

11. The process of claim 8 wherein said aliphatic polyamine is a member selected from the group consisting of ethylene diamine and diethylene triamine.

12. Mild-to-the-skin liquid washing, dishwashing and cosmetic cleansing agents having a content of from 10% to 70% by weight of at least one mild-to-the-skin salts of anionic tensides of claim 1, and the remainder conventional liquid washing, dishwashing and cosmetic cleansing agent ingredients.

13. In the process for the washing of hand washable textiles, dishes and human skin and hair comprising utilizing a washing solution containing a mild-to-the-skin anionic tensides and rinsing said hand washable textiles, dishes and human skin and hair, the improvement consisting of utilizing the mild-to-the-skin salts of anionic tensides of claim 1, as said mild-to-the-skin anionic tenside.

* * * * *